US008566189B2

(12) United States Patent
Sutter et al.

(10) Patent No.: US 8,566,189 B2
(45) Date of Patent: Oct. 22, 2013

(54) COMPUTER-ENABLED METHOD AND SYSTEM FOR FACILITATING VETERINARY PHARMACEUTICAL AND OTHER ANIMAL-RELATED PRODUCT TRANSACTIONS

(75) Inventors: Donald C. Sutter, Tulsa, OK (US); Kurt D. Green, Tulsa, OK (US); Thomas A. Friar, Portland, OR (US); Andrew J. Bane, Portland, OR (US); Sara C. Davis, Portland, OR (US)

(73) Assignee: Strategic Pharmaceutical Solutions, Inc., Portland, OR (US)

( * ) Notice: Subject to any disclaimer, the term of this patent is extended or adjusted under 35 U.S.C. 154(b) by 681 days.

(21) Appl. No.: 12/703,734

(22) Filed: Feb. 10, 2010

(65) Prior Publication Data
US 2011/0196804 A1  Aug. 11, 2011

(51) Int. Cl.
*C07F 19/00* (2006.01)
*G06Q 10/00* (2012.01)
*G06Q 50/00* (2012.01)
*G06Q 30/04* (2012.01)
*G06Q 50/22* (2012.01)
*G06Q 50/24* (2012.01)

(52) U.S. Cl.
CPC ............... *G06Q 30/04* (2013.01); *G06Q 50/22* (2013.01); *G06Q 50/24* (2013.01)
USPC ..................................... 705/34; 705/2; 705/3

(58) Field of Classification Search
None
See application file for complete search history.

(56) References Cited

U.S. PATENT DOCUMENTS

| | | | | |
|---|---|---|---|---|
| 2002/0143434 | A1* | 10/2002 | Greeven et al. | 700/236 |
| 2003/0229452 | A1* | 12/2003 | Lewis et al. | 702/19 |
| 2006/0031100 | A1* | 2/2006 | Huber | 705/2 |
| 2006/0116940 | A1* | 6/2006 | Dippold et al. | 705/35 |
| 2011/0082771 | A1* | 4/2011 | Pritikin et al. | 705/27.1 |

OTHER PUBLICATIONS

Author: www.petcarerx.com; Title of the Article: PetCareRx—Discount Pet Meds; Title of the item: www.petcarerx.com/perx/default.aspx; Date: copyright notice date on webpage 1998-2010; p. 1-3 (copy attached for convenience); Publisher: www.petcarerx.com; City and/or Country: World Wide—Internet.

Author: www.petmedsonline.org; Title of the Article: Pet Health Products for Dogs; Title of the item: www.petmedsonline.org/pet-health-meds-for-dogs.html; Date: copyright notice date on webpage 2006-2008; p. 1-2 (copy attached fro convenience); Publisher: www.petmedsonline.org; City and/or Country: World Wide—Internet.

(Continued)

*Primary Examiner* — Ryan Zeender
*Assistant Examiner* — Denisse Ortiz Roman
(74) *Attorney, Agent, or Firm* — Howard Russell

(57) ABSTRACT

A computer-enabled method and system for generating a script for veterinary pharmaceutical and other animal-related product transactions comprising aggregation of participant data, including animal hospital data, veterinarian data, client data and animal data into the script, adding treatment regimen data to one or more orders associated with the script in accordance with the veterinarian's treatment plan, to enable determination of the initial date to begin filling the product, quantity of product, the number of fills and frequency to enable automatic generation of a series of autoship records including projected dates for shipping the orders to the animal owner upon verification of funds available, to print usage instructions, Rx labels, product information, shipping labels and packing slips, and to send notification emails to the animal owner and confirmation emails to the animal hospital.

12 Claims, 9 Drawing Sheets

(56) References Cited

OTHER PUBLICATIONS

Author: www.1800petmeds.com; Title of Article: America's Pet Medication & Pet Supplies Pharmacy; Title of the item: www.1800petmeds.com/index.jsp?AFFID=GG&ID=159441817; Date: First Use Date for 1-800-Petmeds Registered Trademark listed as Jun. 1, 2002, no date found on webpage; p. 1-2 (copy attached for convenience); Publisher: www.1800petmeds.com; City and/or Country: World Wide—Internet.

Author: www.drsfostersmith.com; Title of the Article: Pet Supplies, Dog & Cat Supplies, Pet Meds; Title of the item: http://www.drsfostersmith.com/?ref=4397&subref=AA&mkwid=SYquxiB03IperidI4170952971&cmpid=PPC-__-G__-4397; Date: copyright notice date on webpage 1997-2010; p. 1-4 (copy attached for convenience); Publisher: www.drsfostersmith.com; City and or Country: World Wide—Internet.

* cited by examiner

COMPUTER-ENABLED METHOD AND SYSTEM FOR FACILITATING VETERINARY PHARMACEUTICAL AND OTHER ANIMAL-RELATED PRODUCT TRANSACTIONS

BACKGROUND OF THE INVENTION

The present invention relates in general to managing the distribution of veterinary pharmaceuticals and other animal-related products and in particular to a computer-enabled method and system for facilitating, managing and controlling prescription generation, subsequent processing of the prescription, and dispensing, fulfilling and delivering of animal products according to a veterinarian treatment plan.

FIG. 1 illustrates the traditional and often repeated scenario of an animal owner that has brought an animal, such as a pet, to a veterinarian at an animal hospital, including any animal treatment facility or location where a licensed veterinarian is authorized to do business, for treatment of a condition as shown at 10 to respond to illness of the animal or improve the animal's health. Once the veterinarian has examined the animal, and based on observations and medical experience, the veterinarian communicates a verbal treatment plan as shown at 12 and issues a written prescription to the owner as shown at 14. FIG. 1 also illustrates that compliance to fulfill the script at 16 and to administer treatment to the animal at 20 in accordance with the treatment plan has been almost exclusively dependent upon the animal owner.

However, this traditional method of treating animals with animal-related products has been subject to the primary shortfall of non-compliance of administering the recommended treatment to the animal as illustrated at 26, 28. Largely, such noncompliance has resulted from inherent delay and the inconvenience placed upon the owner to return to the veterinarian to renew prescriptions, to hand-carry prescriptions to the local pharmacy, wait to have them filled, and to remember to administer the treatment as prescribed to the animal according to the treatment plan. Thus, non-compliance may include any deviation from the treatment plan of the veterinarian, such as an owner's failure to renew the prescription, failure to refill the prescription and do so in a timely manner as shown at 22, or failure to administer the treatment and do so in a timely manner according to the treatment plan as shown at 26, 28. Since the animal has been mostly unable to indicate need for treatment, compliance has been left primarily to the owner in this traditional scenario, and diminished compliance has resulted.

In the case of treatments that have involved the administration of multiple doses of medicine or supplement on a periodic basis, for example weekly, in the past the owner has had the option of purchasing an initial quantity of medication or supplement sufficient for the entire anticipated treatment period, to be administered in multiple subsequent periodic installments at the sole remembering and initiative of the animal owner. Or, in the case of ongoing treatments over time, the animal owner might have been required in the past to return to the veterinary pharmacy for filling of subsequent installments of treatments prior to the owner's having administered such subsequent treatment to the animal. But as shown at 22 and 26, neither the return to the pharmacy, and as a result, nor the administration of the treatment occurred, illustrating noncompliance with the treatment plan.

It is distressing that there has been a very low compliance rate in the administration of pharmaceuticals to animals, documented as between 34-48 percent among customers of veterinary preventative medications, and 19% for therapeutic diets, as published in the 2003 AAHA study, *The Path to High-Quality Care: Practical Tips for Improving Compliance*. Low compliance has also been due, in part, to the fact that there has not been implemented an effective delivery strategy for veterinary supplies to allow convenient and efficient application of the product to the animal.

Traditional prior art methods and systems of dispensing veterinary pharmaceuticals have not employed effective means for veterinarians and their staff to positively impact compliance of the animal owner in using the prescribed medication or supplement, leading to less effective treatment outcomes. Furthermore, prior non-computerized methods and systems of enabling, controlling and managing the processing, fulfilling and dispensing of veterinary pharmaceuticals and animal-related products have negatively impacted the ability of veterinarians and animal hospitals to effectively participate in the distribution of such products. Thus, these prior systems and methods have negatively impacted the ability of veterinarians and veterinary hospitals of varying sizes, from smaller to larger hospitals, to effectively participate profitably in the sale directly to customers of the increasingly larger varieties of products available. This has been in part due to the fact that it has been very difficult for the veterinarians and veterinary hospitals to maintain sufficient quantity of a sufficient number of different types of pharmaceuticals and supplements in inventory at the veterinarian's site, without these becoming outdated due to limited numbers of sales.

Furthermore, traditional manual pharmaceutical and supplement order, fulfillment and dispensing solutions, requiring separate trips by the animal owner to the pharmacy, have not allowed the sale of the animal-related products in such a way as to provide a smooth and efficient transaction from the perspective of the veterinary hospital and the animal owner.

Attempts have been made to address some of the foregoing basic limitations of manual ordering, fulfillment and dispensing systems, as with a typically customer-centric, centralized pharmacy accessible by the customer, or alternatively the veterinarian, by telephone or the Internet. Such systems have enabled improvements, allowing greater ease for the animal owner to access the pharmacy via telephone or Internet, and hence there has been slightly less likelihood of delay in fulfilling scripts. Also, in such cases, as with previously described methods and systems, sometimes the veterinarian has been able to call in, fax in, or email in a script directly to the pharmacy for manual pickup by the customer. Nevertheless, these prior art solutions have lacked a coherent strategy and computerized system for controlling and managing the script-writing, ordering, fulfillment and delivery of pet products in such a way as to enhance compliance with veterinary treatment plans and incentivize involvement in the ongoing treatment of the animal by the veterinarian and hospital.

Such systems have not been well designed to account for the fact that, in order for a veterinarian to issue a script, he or she must first see the animal for which the treatment plan is issued. Therefore, while the telephone or Internet enabled model of distributing veterinary pharmaceuticals has facilitated the distribution of medicines, it still has lacked a viable method for the creation of effective animal treatment plans by a veterinarian that has seen the animal. Of course, a veterinarian could call a remote pharmacy and place a medication order, and that order could be shipped to the customer, but this method has required an additional step for the veterinarian to send the script to a remote pharmacy because there is no comprehensive system for managing the process, including a comprehensive system for fostering an economic incentive for the veterinarian to call a particular pharmacy. In fact, there may have been a disincentive for this relationship, because once the customer has been introduced to the pharmacy with this method, the pharmacy could have developed, and frequently has developed, a direct relationship with the animal owner, selling additional products and services with no economic benefit to the veterinarian.

Since the animal owner could easily call and order a product online or over the telephone with such prior art methods and systems, there has been some incentive to fill a prescription without a veterinarian actually seeing the animal. While such practice may have been temporarily convenient and may have cost less in the short run for the pet owner, such practice has been considered by the American Veterinary Medical Association to not be appropriate, unless a prescription is issued in the context of a veterinarian-client patient relationship. This means that there must be a valid relationship with a veterinarian who has examined the animal in order for them to prescribe medication for the animal. Since legally a pharmacy cannot provide prescription medication itself without a veterinarian prescription, there has been incentive in the past by a remote pharmacy to substitute supplements for the animal that have not required a prescription. It's clear that prescription drugs have been most efficacious for treating animals, and the non-prescription alternatives have been less so. All of these factors highlight the inherent potential conflict of interest that exists between online veterinary pharmacies and veterinarian hospitals.

Further, such systems have done little to improve the compliance of administering pharmaceuticals and supplements in accordance with a veterinarian-prescribed treatment plan, since in such case treatment has still been left almost exclusively to the animal owner.

There is currently a very large number of supplement and pharmaceutical treatment options available for animals and the wide variety of disorders and conditions they have presented. Accordingly, it has been very difficult, if not impossible, for a veterinarian, or a small veterinary hospital, to have maintained in stock sufficient quantities of each of the many and varied medications available, without such supplies becoming stale, losing potency, or expiring. This is because a smaller veterinarian practice or hospital would not see the number of animals necessary to effectively maintain a robust compliment of the many treatment options currently available. Further, the management of such inventory, even if possible, would be very cumbersome, labor intensive, and loss of revenue due to the need to appropriately discard expired medication has been significant.

While the foregoing clearinghouse-type centralized pharmacy solutions have sought to address this dilemma faced by veterinarians, as described above, the solutions have entailed other problems, have not addressed compliance issues as described, and have not adequately involved the veterinarian in the process or transaction sufficient to ensure the high-quality treatment that owners expect for their pets and other animals.

Also, these prior art systems have not addressed the need for an effective means of controlling and managing the script writing process itself. While it would be advantageous to allow non-veterinary-doctor associates, veterinary assistants, to make preliminary selections of medications or supplements for a particular treatment situation, for later approval by a veterinarian, this has proven difficult to accomplish in real time with manual script generation processes in a busy hospital situation, since a veterinarian would need to be in more than one place at one time to approve many different scripts before each customer leaves the premises. In practice, what has happened in the past at busy pet hospitals, is that a veterinarian might spend the morning portion of his or her shift reviewing charts and unsigned scripts, tediously calling to awareness the details of each individual chart before approving the script, and so forth, until each script has been signed, often after the customer and its animal have already left the hospital.

There has been lacking with prior art attempts a means of efficiently updating veterinarians and hospital staff with new product offerings and training in such a way as to make this information easily available to the veterinarian at the point of prescribing. This, in turn, has made it more difficult for the veterinarians to keep up with advances in products and types in order to be able to pass the benefits of the new products on to their customers.

Further, as a result of the limitations of prior art veterinary pharmacy methods and systems that have not provided for an integrated, computerized script generating and processing capability at the point of customer advice, consult and interaction with the veterinarian, the veterinarian has been less able to be present during instruction to the customer and ordering in order to resolve discrepancies. This, in turn, has resulted in a more costly, less efficient system overall, and furthermore has resulted in a lack of access to and control by the hospital over the transaction. This has been very costly to the veterinarian and hospital in the past, because they have not been able to effectively dispense the wider array of medicines and supplements available to the larger centralized pharmacies that dispense by mail directly to the customer. Not only has this adversely impacted the ease of the veterinarian to provide care, but also has made it virtually impossible for the veterinarian to participate in the transaction financially. One result of this lacking has been a lower rate of compliance in administering the medicine to the pet, simply because the veterinarian has not been involved in the transaction and there have not been adequate reminders in place for the customer.

Without a script writing and control system integrated into the order and fulfillment system, prior art providers are left to make product information available to the veterinarian doctors in the way of advance-sheet product descriptions and pharmaceutical sales representative account services. This is inefficient compared to an integrated system and leaves more to chance the hope that the veterinarian, or even less likely the staff member, will remember a particular medicine alternative, of many such alternatives including possible generic options, at the point of presenting the option to the customer.

Yet another limitation of the prior art pet pharmaceutical and supplement supply system has been that veterinarians and staff have had limited animal and medicine data readily available to work with to enable easier and more accurate creation and processing of a script. This, in turn, makes it more difficult to efficiently prescribe the right dosage and type of medication based upon detailed animal data accessible through a data repository. With prior art methods and systems, the veterinarian has had to tediously call to attention all of the details of the treated animal's history by manually reviewing the animal's hard-copy, printed file before prescribing a treatment regimen.

SUMMARY OF THE INVENTION

In accordance with an aspect of the present invention, a computer-enabled method is provided for the processing, dispensing, fulfillment and delivery of at least one order for veterinary medicine. In the method, a licensed veterinarian and an animal hospital are preferably registered with a remote pharmacy, and the method enables the veterinarian to create, view, and modify data from at least one client computer connected over a communications channel to an application server having an attached storage system. Further, the method enables the veterinarian to generate a script and associated orders from veterinarian input and data residing on the storage system of the application server. Thereafter, dispensing is accomplished by the remote pharmacy, and fulfillment is also accomplished by the remote pharmacy for delivery directly to the animal owner.

In accordance with this aspect of the invention, participant data is aggregated into the script via the following steps: retrieving and storing in a computer readable medium at least part of each of the following data elements or types: animal hospital data, veterinarian data, client data, animal data profile. Upon reviewing the animal data profile, the veterinarian is enabled in creating and aggregating participant data into an electronic script that, when aggregation is completed, comprises a reference to the animal hospital data retrieved, a reference to the veterinarian data retrieved, a reference to the client data retrieved, and a reference to the animal data retrieved.

With this aspect of the invention, the veterinarian is supported in efficiently creating treatment plans and associated scripts in that he or she does not have to rely upon opening a physical file to tediously review all the information that needs to go into the participant portion of the script including the appropriate hospital, veterinarian name, customer name and animal name.

In accordance with another aspect of the invention, the veterinarian's treatment regimen is enabled for addition to the script in that preferably the treated animal's profile is displayed and a list of products and supplements are displayed from which the veterinarian may select the desired product or supplement for treatment of the animal. In accordance with this aspect of the invention, at least one order is created associated with the script. Each order created and stored in an orders database comprises a reference to the associated script, a reference to the selected product, added pharmacy notes keyed or otherwise entered by the veterinarian, usage instructions, initial fill date, quantity, fills, frequency and count. Count, is set initially to the number fills (shipments) specified for that particular order. Thereafter, the veterinarian approves the script as complete, and responsive to the veterinarian's approval, the system sets a startdate data field to the current date. A complete status data field initially set to FALSE is also set to TRUE in the scripts database.

This aspect of the invention facilitates the veterinarian's efficient development of a treatment plan and capturing those portions of the treatment plan necessary to be included in the script. Since the animal's profile and historical information about previous treatments are able to be viewed in conjunction with the selection of products from a list of products, the veterinarian's job is made easier, thus making the veterinarian more efficient and profitable in his or her practice. Additional support in devising and calculating an effective treatment plan may be provided, since a script date is provided, initial ship date, quantity, number of fills and frequency are able to be entered, retained and automatically calculated to ultimately create a schedule, or series of autoship records, for delivery of products selected by the veterinarian.

Further, this aspect of the invention allows the veterinarian to be virtually automatically reminded of newly available product treatment options, and the veterinarian is incentivized to provide a better treatment option for the animal, since a wider variety of selections of treatment options are made conveniently available to the veterinarian at the time of creating the script.

The participant aggregation and treatment regimen generation aspects of creating an electronic script manage the script creation process and serve to save the veterinarian and the animal hospital time, and therefore money, by allowing scripts to be processed individually or as a group of scripts, the veterinarian being able to sit down at a terminal to more efficiently consider a larger number of cases. Further, this aspect of the invention enables a veterinarian's staff members to assist by populating a script with suggested participants for later approval by the veterinarian, thus saving the veterinarian time and enabling the veterinarian to practice more profitably.

In accordance with another aspect of the invention, autoship records are generated for each order. An order from the orders database having a count greater than zero and that is associated with a script having a complete field set to TRUE is retrieved into a computer readable medium. Each autoship record is given a unique autoship ID number, script data including at least a script ID number from the order is retrieved and stored into the autoship record, and order data including at least an order ID number from the order record is retrieved and stored into the autoship record. Provision is made for inclusion of a reference to a unique supplier ID number (initially set to zero) to be modified later during the autoship delivery process. The value in the remaining autoship record data field is set to count minus one, and the ship date is calculated and stored in the shipdate field of the autoship record. Thereafter, the completed data field of the autoship record is set to FALSE and the autoship record is returned to the autoships database. The value order count is decremented by one in the count data field of the order record, and the updated order record is returned to the orders database. The steps of the autoship generation process are repeated until the value stored in the order count data field in the order record equals zero.

The shipdate calculated in the aforementioned aspect of the invention is computer-calculated according to a software method further comprising the steps of subtracting the count from fills, multiplying the difference by the frequency, subtracting shipping lead time in days from the result of the previous step, adding the difference to the fill date, storing the result as shipdate for the current order.

Compliance is greatly improved with this aspect of the invention since a schedule of autoship records are created by the system in the autoship database and maintained ready for further delivery processing at appropriately scheduled times to serve as an automated reminder to the animal owner to continue to supply the needed treatment to the animal.

In accordance with yet another aspect of the invention, autoship delivery is enabled by retrieving and storing in a computer readable medium an autoship record having a shipdate matching the current date and a completed status equals FALSE. Billing information is used from the at least part of the data stored in the computer readable medium to verify availability of funds for the client. If insufficient funds are available, the completed field of the autoship record is set to INCOMPLETE, the autoship record is returned to the autoship database, and the steps of the autoship delivery method are restarted. If sufficient funds are verified, a reference to the script found in the retrieved autoship record is used to retrieve the reference to the animal hospital which is in turn used to retrieve at least part of the animal hospital data. The reference to the script is also used to retrieve the reference to the veterinarian which is in turn used to retrieve at least part of the veterinarian data. The reference to the script is further used to retrieve the reference to the client which is in turn used to retrieve at least part of the client data. The reference to the script is yet further used to retrieve the reference to the animal which is in turn used to retrieve at least part of the animal data. A reference to the order found in the autoship record in the computer readable medium is used to retrieve at least part of the order data. A reference to the product found in the order record is used to retrieve at least part of the product data. Everything necessary to process the autoship delivery, including the aforementioned script, order and the data corresponding with the references mentioned above, has now been stored in computer readable medium. Thereafter, at least usage instructions, an Rx label and product information are printed from at least part of the data stored in the computer readable medium. Next, the prescription is dispensed or other product is picked, the supplier ID number is selected from the suppliers database and stored in the supplier ID field of the autoship record indicating the actual supplier used to complete this order, and the autoship record completed is set to TRUE indicating that this autoship record has been processed. Finally, the completed autoship record is returned from the computer readable memory to the autoships database.

Further, in accordance with this aspect of the invention, the steps for autoship delivery are repeated for every autoship record in the database having associated matching client addresses that are scheduled for shipping on the current date. In this way, orders for multiple products to be sent to a single address on the same day are conveniently placed in a single package for shipping. Yet further, in accordance with this aspect of the invention, the package is weighed, postage is calculated, a shipping label is printed and a packing slip is printed.

It will be appreciated that, of course, the steps of this autoship delivery aspect of the invention are repeated for every autoship record in the database, recalling that only those autoship records that have matured, in that their autoship record date matches the current date and the completed field is still set to FALSE, will be further processed for delivery.

This aspect and other aspects of the invention greatly simplify the process for the animal owner, since the animal owner is not required to waste time, money and resources to travel to a local pharmacy and wait to have the script filled by the pharmacist. Rather, since the script is automatically processed at a remote pharmacy, the customer is simply satisfied knowing that a sample provided by the veterinarian will cover the initial application of treatment to the animal while the order is automatically processed for delivery directly to the animal owner's doorstep.

Thus, this aspect of the invention also begins to positively impact compliance rates with veterinarian treatment plans since the animal owner is less likely to put off or forget going to the pharmacy because of anticipated hassle and delay. Since compliance with the veterinarian's treatment plan is not dependent almost exclusively upon one person, the animal owner, as with prior art solutions, compliance is improved with the invention because the animal owner is supported and reminded at appropriate intervals in administering treatment to his or her pet.

Since shipment of subsequent orders to the customer are authorized at the time of treatment, autoship records are automatically generated by the system, and delivery of the products is made at the appropriate time according to a predetermined schedule for delivery and application to the animal so that the animal owner is effectively reminded to carry out the treatment plan, the animal owner is relieved of the need to return to the veterinarian for new prescriptions, except as necessary for the veterinarian to follow up with the animal, and the animal owner is relieved of the need to return to the pharmacy or other pet supply facility for re-fills of the prescription or purchase of other periodically and frequently used animal products, such as supplements. Of course, this also results in better care for the animal and greater compliance with veterinarian treatment plans.

The simplification of the process for the animal owner does not come at the expense of quality of treatment to the animal, since a veterinarian is more incentivized to be more closely involved in developing and following the treatment plan than would be the case with other prior art methods of manual script generation and processing, or than would be the case with telephone or Internet pharmacies. Since the present invention is veterinarian centric, instead of pharmacy centric, the veterinarian is able to better direct the care and treatment of the animal and is also able to participate financially in the transaction. The veterinarian and the animal hospital staff are thus encouraged to work with a particular remote pharmacy, because they know that they will receive prompt, accurate and effective filling and dispensing of products prescribed, without the inherent risk of losing customers and conflict of interest associated with other prior art methods. In the end, these facts lead to better care and treatment for the animal.

Another aspect of the invention recognizes that the remote pharmacy may choose, for any of a number of reasons, to integrate into the delivery process a drop ship supplier, such as a supplier that ships product directly to a client at a request of the remote pharmacy. This aspect of the invention allows the remote pharmacy greater flexibility in using the most efficient, cost effective and convenient method, of filling the order, thus providing greater service to the customer and resulting better treatment for the animal. The system database also serves as a convenient place for ad hoc queries to produce metrics for identifying the most cost effective and convenient supplier and shipping method.

In accordance with another aspect of the invention, a notification email is sent to the client (animal owner) to let them know that their order has been shipped and the treatments are on the way. This notice also serves as a reminder to the client to treat the animal and thus serves to bolster compliance with the veterinarian's treatment plan. Preferably, the animal hospital is also notified so that the hospital's records may be updated and hospital staff may be informed that compliance with the veterinarian's treatment plan has been facilitated. This, together with information already accessible from the system electronically, gives the veterinarian and hospital staff additional information and metrics with which to positively participate in following up with the treatment of the animal.

In accordance with another aspect of the invention, there is provided an automatically updated database listing of available products for the veterinarian to choose from. This aspect of the invention assists the veterinarian in staying currently abreast of a wide array of treatment options for animals and also helps the veterinarian with staying current regarding changes to products and product lines. Further, this aspect of the invention addresses the difficulty experienced by individual veterinarians, small animal hospitals, and even larger ones, to keep in stock an effective quantity of products, eliminating the need for the large financial investment to obtain such a stock and the economic hit and waste associated with expiration of perishable items and their disposal.

Since the veterinarian is conveniently placed at the center of the supply of pharmaceuticals and other products in the processes of the invention, the veterinarian is supported in providing better care to the animal and in enabling better compliance by the animal owner with treatment plans. This coherent, comprehensive, veterinarian-centric method and system of supplying animal-related products to animal owners for administering treatments to their animals fosters appropriate and best practices for practicing veterinarian medicine. From generation of the script to the auto-generation of shipment records and the automated delivery of products to the animal, the veterinarian, the animal hospital, the animal owner and the animal are all supported in a more efficient and seamless strategy for treatment.

The subject matter of the present invention is particularly pointed out and distinctly claimed in the concluding portion of this specification. However, both the organization and method of operation, together with further advantages and objects thereof, may best be understood by reference to the following descriptions taken in connection with accompanying drawings wherein like reference characters refer to like elements.

DETAILED DESCRIPTION

Figure 1:
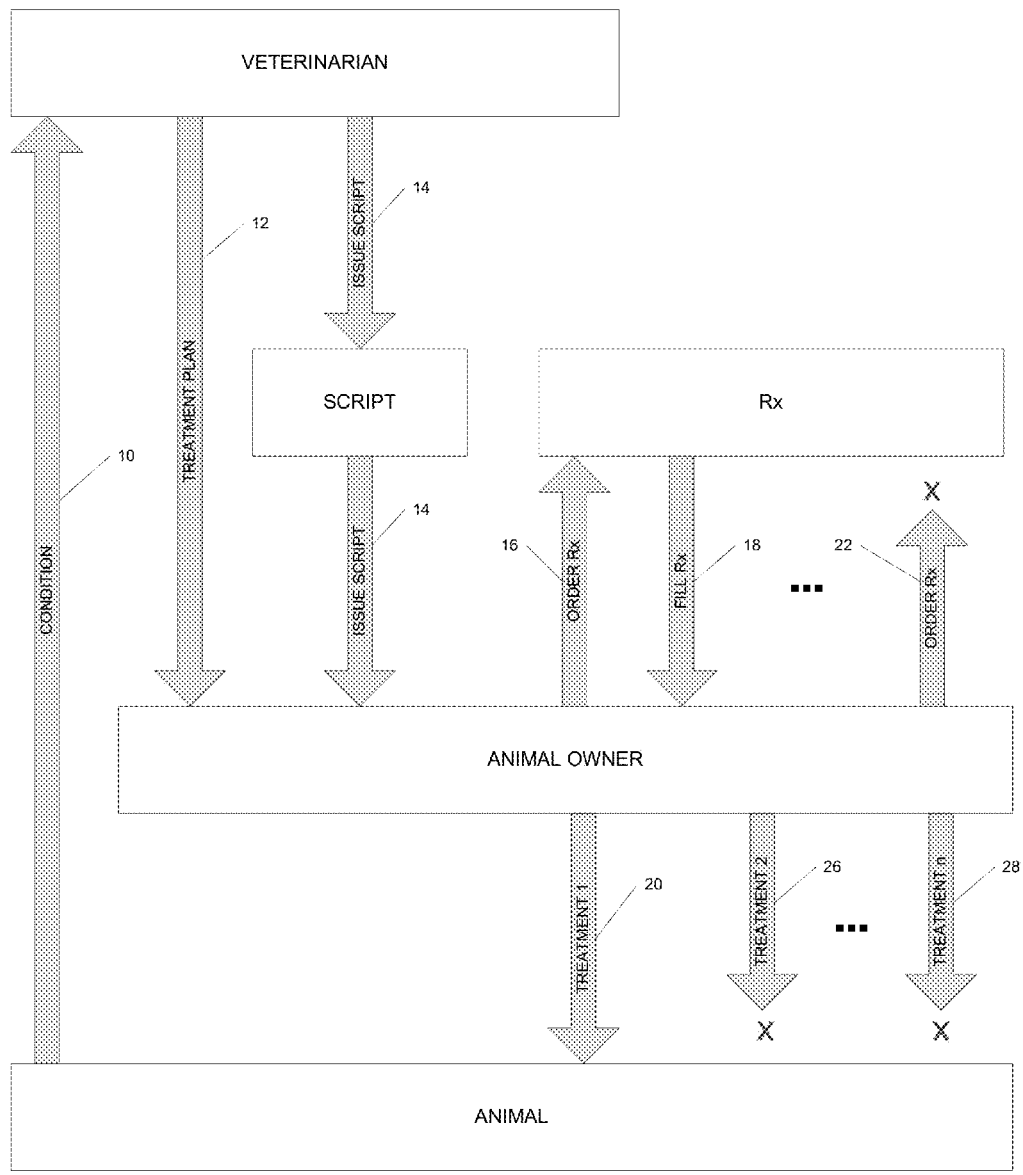
FIG. 1 is schematic representation demonstrating compliance and noncompliance with a veterinarian's treatment plan in connection with a prior art method and system for treatment of animals.
Figure 2:
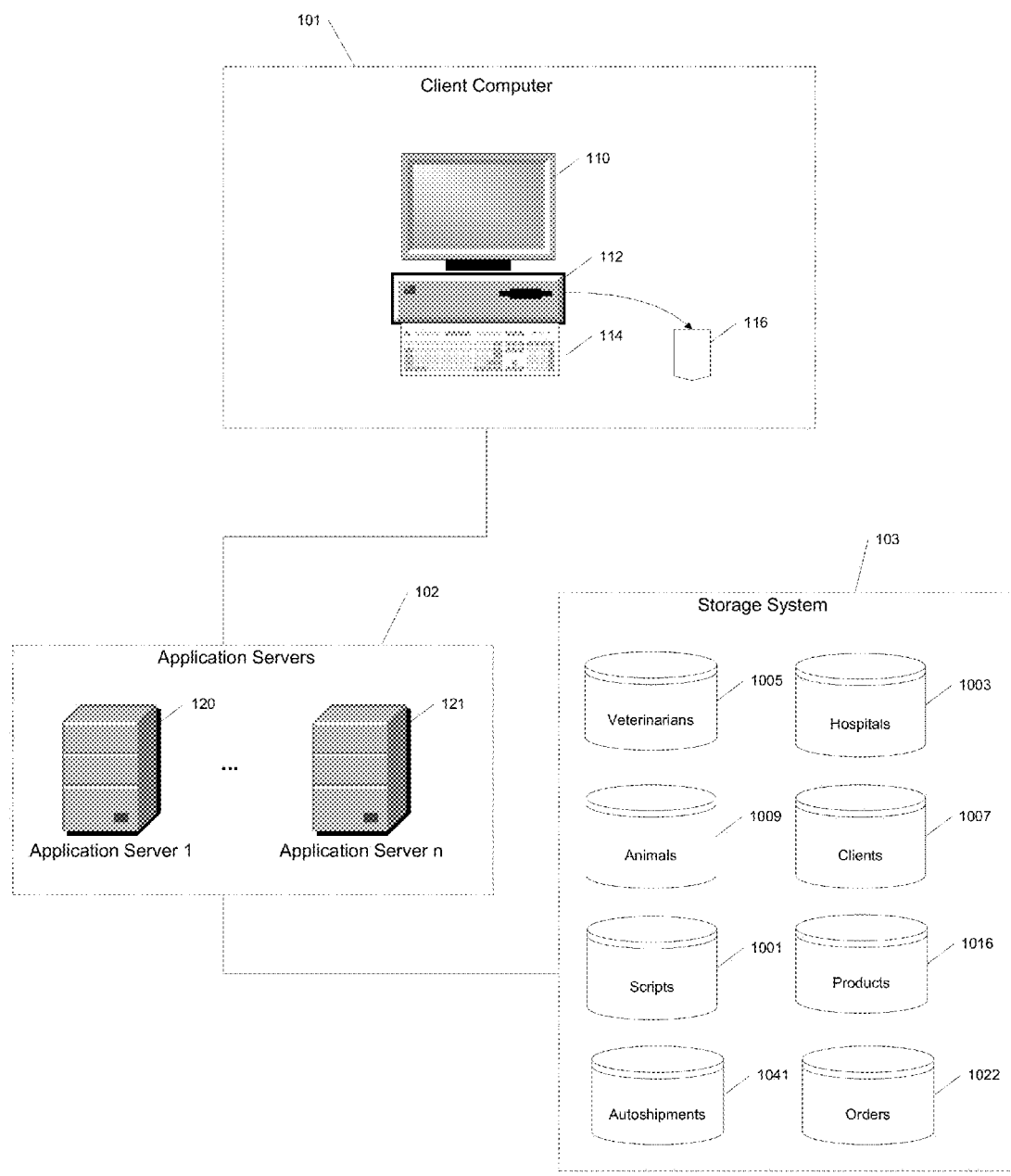
FIG. 2 is a schematic representation of a client server system with a supporting data storage system in accordance with which a preferred embodiment of the invention is practiced.

Referring to FIG. 2, client computer system 101 is one of a plurality of such client computer systems being located at a veterinarian hospital, including any animal treatment facility or location where a licensed veterinarian is authorized to do business, and the server system 102 with supporting data storage system 103 may support many such hospitals having such plurality of client computer systems 101.

While each client computer system 101 preferably comprises a traditional monitor 110, processing hardware 112, keyboard 114, mouse 116, application software, Internet software and hardware components (not shown), it will be appreciated by those of ordinary skill in the art that any computer system, such as a smart phone, hand-held device, laptop, or other equivalent computing device with adequate memory and processing capability will satisfy the client computer system for purposes of the present invention. Further, multiple client computer systems 101 may be networked, for example on an Ethernet-type network within a Hospital complex, the networked systems being represented in whole by client computer system 101 as is well understood by those of ordinary skill in the art. Further, it will be appreciated by those of ordinary skill in the art that, since many veterinarians work independently, the invention may be used by individual veterinarians by considering the veterinarian and the hospital to be one and the same in the database.

Client computer systems 101 may run any type of client computing operating system and software, such as Windows®, that enables access by the user of the client computer system to the Internet and the ability to process application data within the client portion of the application software of the invention on the client computer system.

One or more application servers 102, comprising parallel processing, mirrored, or RAID configured servers 120, 121, etc., run the server side portion of the application software of the invention and provide secure access to data in the storage system 103. Servers 102 may comprise a plurality of servers that are housed in a single location where the size of the system permits and there exists sufficient power and security to meet reliability and availability needs. The servers 102 are preferably interconnected to each other and to data storage system 103 by a high-speed local networking system. Servers 102 are also connected to the plurality of client computers 101 via the Internet.

Storage system 103 preferably comprises a redundant array of magnetic storage media disk drives, optical storage system, or the like, capable of the fast access and retrieval times necessary to accommodate many requests in rapid succession from the multiple client computer systems 101 and application servers 102.

Storage system 103 houses a plurality of databases corresponding with key elements of data preferable for the completion of a script, each script potentially further comprising a plurality of orders to be processed into a plurality of autoship records for fulfillment and shipping by a central pharmacy. The key elements of data preferable for the completion of a script comprise scripts data 1001, hospitals data 1003, veterinarians data 1005, clients data 1007, animals data 1009, products data 1016 and orders data 1022. Thus, as will be appreciated by those of ordinary skill in the art that all of the above-mentioned elements of a script are required for a completed script.

Figure 3:
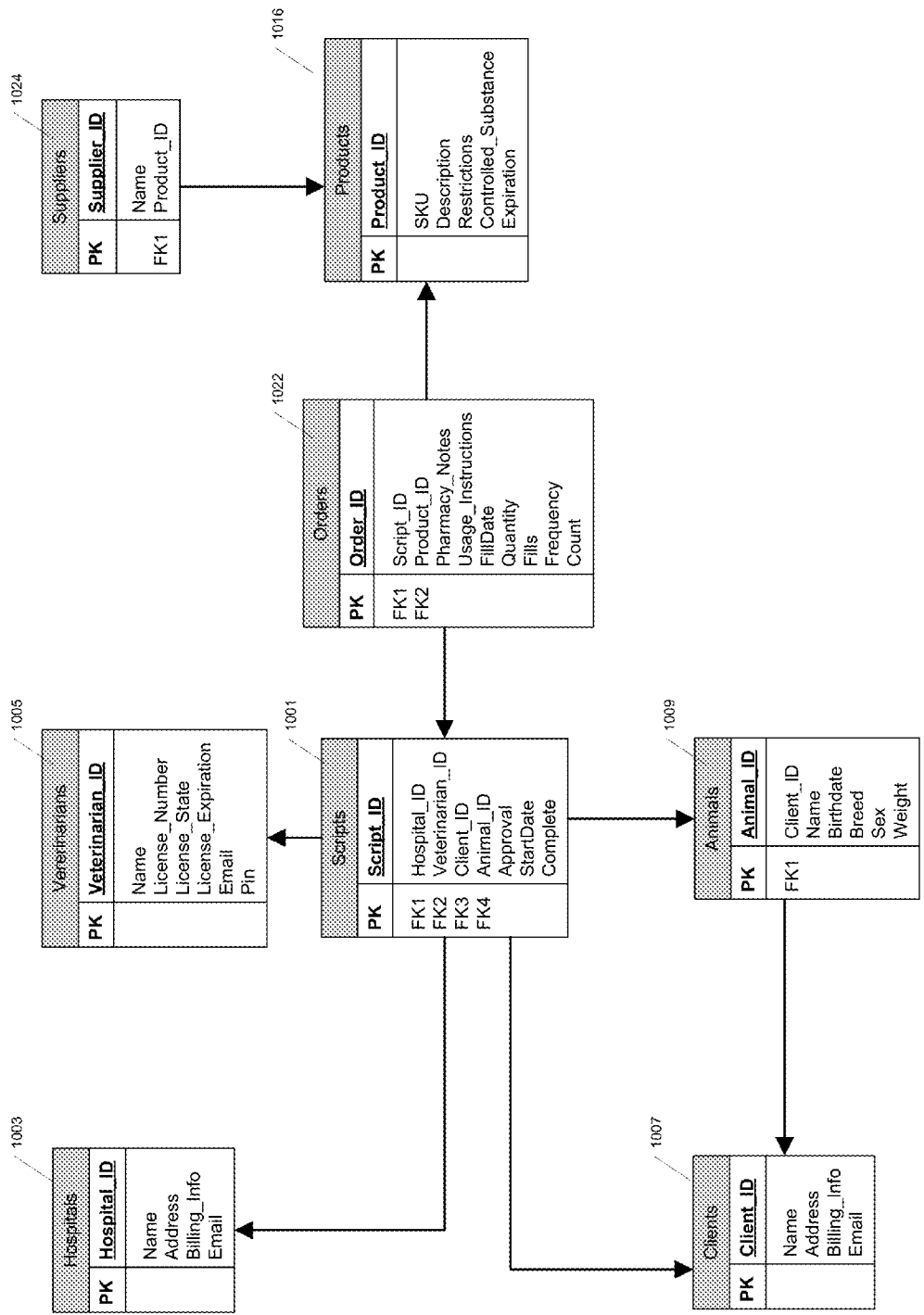
FIG. 3 is an entity relationship diagram illustrating an aspect of the invention comprising a self-synchronizing relational database showing the interrelationship between key elements of a data structure in accordance with a preferred embodiment of the present invention.

Referring to FIG. 3 illustrated in database entity relationship diagram notation, an aspect of the invention comprises a data structure residing in a self-synchronizing relational database, such as in a Structured Query Language database server, preferably comprising interrelationships between identified elements as shown, and wherein a plurality of scripts 1001, each script being represented by a unique script ID number and being first partially completed with participant information such as a hospital ID number from hospitals data 1003, a veterinarian ID number from veterinarians data 1005, a client (e.g., animal owner) ID number from clients data 1007 and an animal ID number from animals data 1009.

FIG. 3 shows that each script ID number is associated with a hospital ID number, veterinarian ID number, client ID number, animal ID number, veterinarian approval (electronic signature), date/time stamp and completion status as TRUE or FALSE (e.g., complete or incomplete respectively). Each hospital ID number is associated with a hospital name, address, billing information and email address. Each veterinarian ID number is associated with the veterinarian's name, veterinary license number, license state, license expiration, email address and authorization pin number which acts as a password to secure the veterinarian's account. Each client (animal owner) ID number is associated with the client's name, address, billing information such as credit card payment details, and email address. Each animal ID number is associated with a client ID number, animal name, birthdate, breed, sex and weight. Of course, those of ordinary skill in the art of database design, programming and veterinary medicine and practice management will appreciate that any additional information specific to a hospital, veterinarian, client, and/or animal, may be contained in its associated database for storage, edit or retrieval referencing that element's unique ID number. A benefit of this design, wherein a record in the database referenced by its ID number, any data retrieved represents the most current version of the data found in the database.

Further, as shown in FIG. 3, each order ID number is associated as shown at 1022 with a particular script ID number, a particular product ID number, and further comprises pharmacy notes, usage instructions, initial ship date, quantity, fills, frequency and count. Each product ID number, in turn, further comprises, as shown at 1016, an associated supplier ID, a SKU number, product description, restriction data, controlled substance indication, and expiration data. Each supplier ID number is associated with a supplier name as shown at 1024.

As will be apparent to those ordinary skill in the art, only the key elements of each orders, scripts, products and suppliers database have been shown and described, and it will be apparent to such persons that these records may be expanded to include additional pertinent information about the unique items each database describes.

Figure 4A:
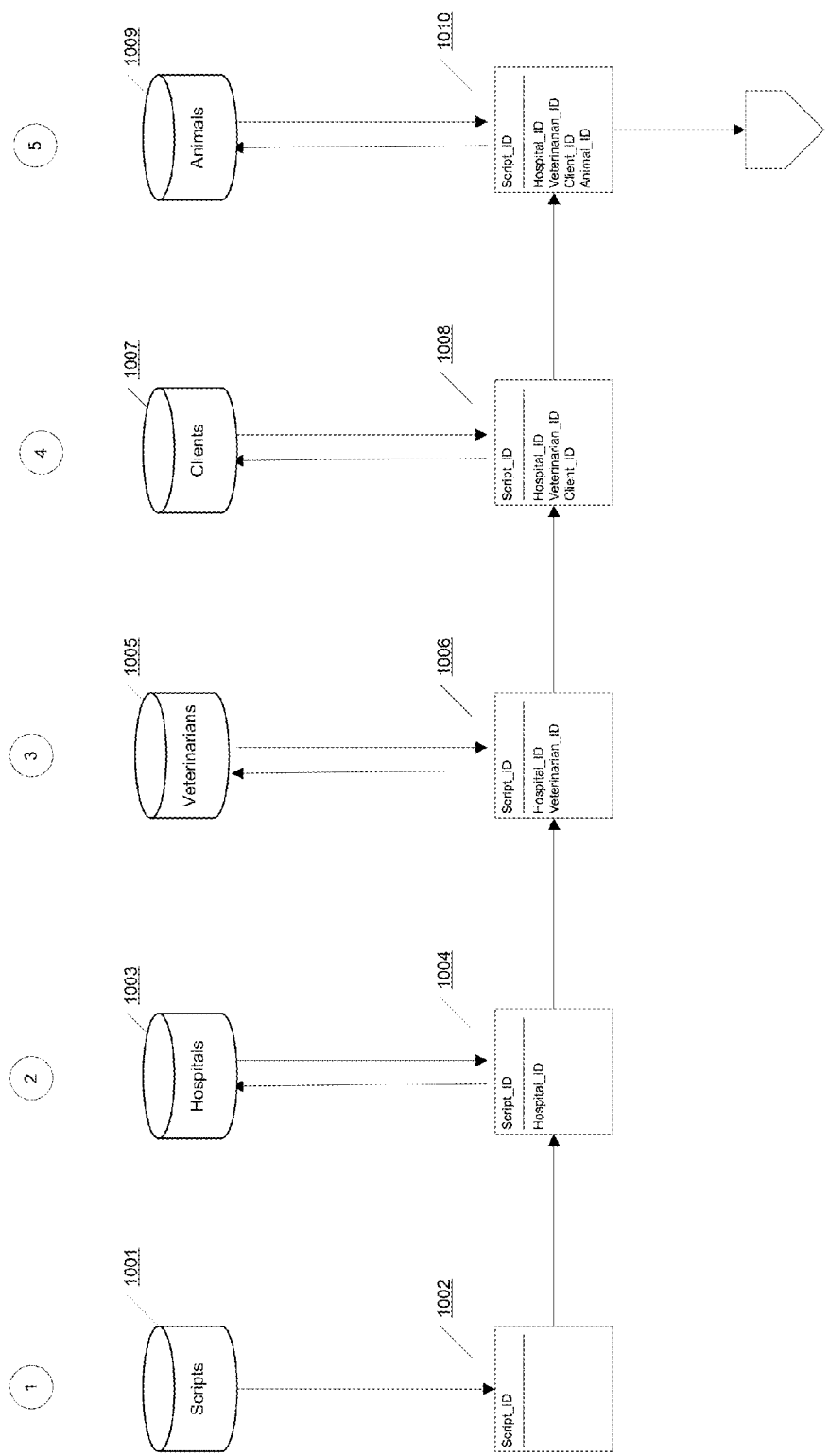
FIG. 4a is a schematic representation of an aspect of a preferred embodiment of the present invention comprising a computer process of generating a script and aggregating of participant data into the script.

Referring to FIG. 4a, a series of steps, suitably performed in the order illustrated by step notations ①  through ⑤, serves to retrieve (or create) a script participant data structure into computer readable medium. The steps ① through ⑤ are preferably, but not necessarily, performed in the order shown. Each step adds a new data element to the script during the process of building the participants aspect of the invention. Thus, the steps in a preferred order are as follows: ① a script is generated from a template retrieved from a data repository 1001 into computer readable medium, the instance of which is shown at 1002 identifying it with a unique script ID number; ② access is made to the hospitals data repository 1003 to retrieve at least a part of animal hospital data, preferably at least a unique hospital ID number, reflecting the hospital where the veterinarian making the script practices veterinary medicine, in order to aggregate it with the Script ID number as shown at 1004 in computer readable medium; ③ a unique veterinarian ID number from a veterinarians data repository 1005 is added to the script in computer readable medium as shown at 1006, reflecting the currently logged in veterinarian; ④ a unique client (animal owner) ID number is pulled from a clients data repository 1007 to be aggregated with the previously associated data as shown at 1008 in computer readable medium; and ⑤ an animal ID number is obtained from an animals data repository 1009 and combined with the other aforementioned data elements in the script in computer readable medium as shown at 1010.

Thus, as shown at 1010, an aggregated script comprises a unique script ID number, hospital ID number, veterinarian ID number, client ID number and animal ID number to complete the facilitation, management and control of the transaction participants aspect of the present invention.

Figure 4B:
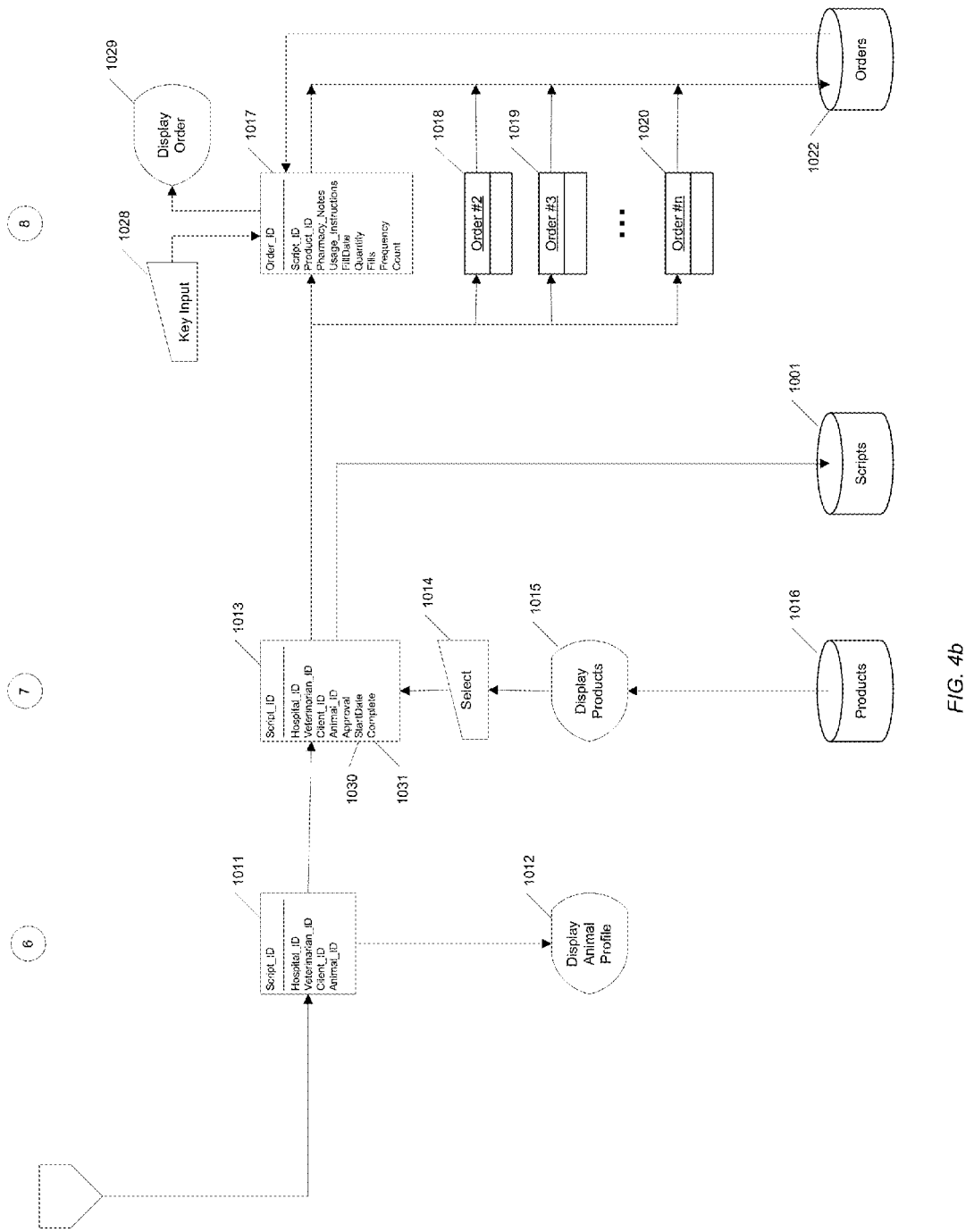
FIG. 4b, a continuation of FIG. 4a, is a schematic representation of another aspect of a preferred embodiment of the invention wherein the veterinarian references an animal's profile, references and selects specific products, and adds the selected products to orders associated with the script.

Referring to FIG. 4b, the treatment regimen creation aspect of the invention is illustrated, wherein animal profiles are reviewed, available medications are reviewed and a selected product is added as treatment data to the participant data previously included in the script. In this treatment regimen creation aspect of the invention the following additional steps are performed: ⑥ animal (e.g., pet) profile information is displayed, retrieved and considered by the veterinarian as necessary or desirable as shown at 1012; ⑦ the veterinarian accesses the product data repository 1016 through a visual display 1015. From the products listed on the display 1015, the veterinarian selects/includes, at 1014, an appropriate product for inclusion in an order; ⑧ as shown at 1017, once a product is selected, an order is generated from a template received from a data repository 1022, an instance of which is shown at 1017, comprising a unique order ID number. The order 1017 also includes the product ID number of the product selected in step ⑦ and the script ID number. Afterwards, responsive to display input 1029, the veterinarian provides key input 1028 including initial fill date (the date of first fill, allowing the veterinarian to specify a delayed the first date for shipping to account for samples provided or other treatment factors), quantity (e.g., the total number of pills to be included in a single shipment), fills (e.g., the total number of shipments for this order), frequency (e.g., the time interval between shipments) and count (a temporary value used to track autoship record generation). Continuing with step ⑧, also as shown at 1017, the veterinarian issues notes to the pharmacy and usage instructions, all in accordance with the veterinarian's treatment plan.

Steps ⑥ through ⑧ of the process are repeated for the same script until all orders for that script are completed (e.g., as shown at 1018, 1019, and 1020), each order containing a unique order ID number and a unique product ID number in accordance with each newly selected product by the veterinarian in step ⑦. Thereafter, or intermediately, other scripts may be generated and either immediately completed, or later completed as necessary to accommodate the veterinarian's workflow. Thus, a single script may be associated with a plurality of orders as shown in FIG. 4b. In an actual implementation of the invention, the foregoing steps would take place simultaneously at multiple client computer systems in multiple hospitals, via the Internet or other network connections or communication channels, at geographically diverse locations. Thus, in order to process numerous transactions simultaneously, the server and database system of the invention must be scaled appropriately to the anticipated usage.

Once a veterinarian has completed a script and its associated orders according to steps ① through ⑧ described above, he or she flags the script as completed through use of the keyboard or mouse. Thereafter the script is date/time stamped as shown at 1030 and the completed flag as shown in 1031 is set to TRUE. At this time the scripts database 1001 contains the current completed record and the orders database 1022 contains one or more orders associated with the script. Thus, the veterinarian has completed the script generation process, and the remote pharmacy will dispense and fulfill the orders in accordance with the invention.

Figure 5:
FIG. 5 is a schematic representation of another aspect of a preferred embodiment of the invention comprising a computer process for the automatic generation of a plurality of autoship records.

Referring to FIG. 5, the autoship generation process 1040 of the invention is used to create, programmatically, autoship records according to treatment plans embodied in associated scripts and orders. The autoship generation process 1040 accesses the scripts database 1001 and the orders database 1022 to generate one or more autoship records for each order. Each order may require one or more individual autoship records, and each autoship record represents one shipment. Since each script may comprise multiple orders, and each order may require multiple shipments, each order potentially requiring a different interval between shipments (frequency), it follows that, according to a given treatment plan in a script, an autoship shipment schedule may involve a complex series of calendar dates necessary to ship products at appropriate times in order to support and maintain compliance with the treatment plan. To allow timely application of a product to an animal according to the veterinarian's treatment plan, the ship date generated by the autoship generation process must account for additional shipping and handling time to deliver the product to the client.

The autoship record generation process may be batch-processed at a predetermined time (e.g., end of the day) or triggered when the script is flagged as complete (e.g., set to TRUE) by the veterinarian. In any event, the autoship process will only create autoship records for those scripts that have been completed by the veterinarian, and not scripts that are only partially completed. Furthermore, the autoship process is executed once, and only once, for each script. Execution of the autoship process on a script may be determined by the presence of an associated autoship record in the autoship database.

As illustrated in FIG. 5, autoship database 1041 comprises a plurality of autoship records. Each autoship record has a unique autoship ID number that is associated with a script ID number, order ID number, supplier ID number, fills remaining (the number of shipments to be made beyond the current shipment), ship date (the target ship date when the order will be shipped) and completed status (a flag in the database changed from FALSE to TRUE when the order is shipped). Those of ordinary skill in the art will appreciate that, though the autoship record does not contain participant data directly (i.e., hospital, veterinarian, client or animal data), such data is readily accessible in its most recent and updated form by using the script ID number to recall the participant ID number, which participant ID number may, in turn, be used to recall the actual record of the participant desired, including its associated data. Thus it will be appreciated that only those parts of data necessary to perform the desired function are retrieved and may be stored into computer readable medium.

Figure 6:
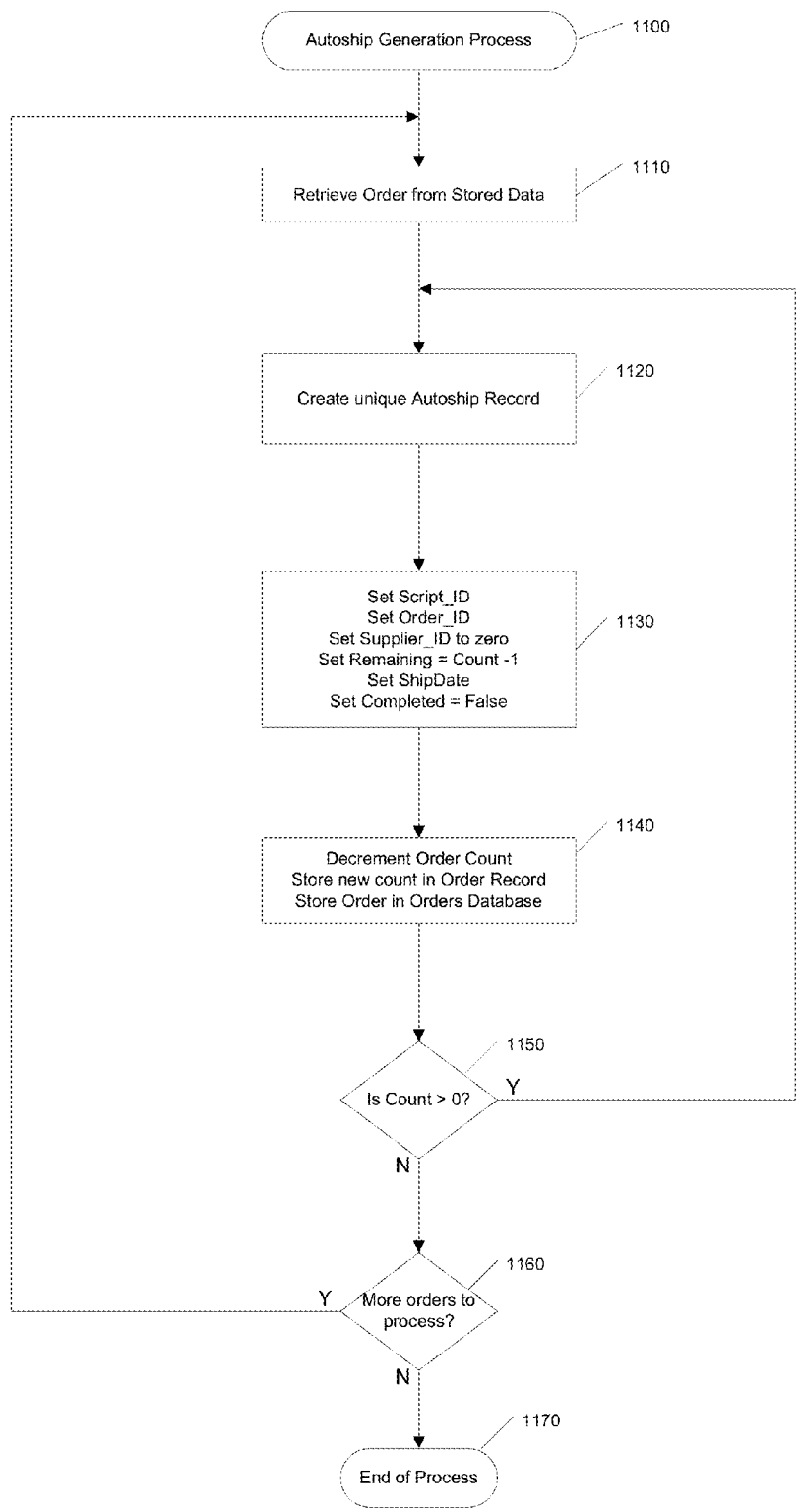
FIG. 6 is a computer program flow chart of the autoship generation aspect of the invention.

Referring to FIG. 6, in the autoship generation process 1100 the system generates a plurality of autoship records based upon completed scripts with one or more associated orders that have not been processed. The autoship generation process 1100 is executed either upon a trigger event due to completion of a script or at a predetermined time as a batch process, provided there are scripts with associated orders to be processed. An order is available for processing when a script record has its complete field set to TRUE and one or more orders associated with the script has a count field that is greater than zero. At 1110 an order is retrieved into a computer readable medium for processing. At 1120, the autoship generation process creates an instance of an autoship record based upon the template found in the autoship database 1041, and the autoship record is assigned a unique autoship ID number. At 1130 the associated script ID number, the associated order ID number, the remaining count minus one (to show the number of additional shipments that will be shipped after this specific shipment is delivered) and the shipdate are stored in the autoship record created at 1120 and the completed field is set to FALSE as this order has not yet been processed for delivery.

Further, at 1130 the shipdate is calculated to determine the date this order will need to ship from the remote pharmacy to allow for shipping and handling time sufficient for delivery to the client just before the treatment is to be administered to the animal in accordance with the veterinarian's treatment plan.

As an example, the shipdate may be calculated according to the following formula:

$$shipdate = filldate + ((fills - count) * frequency) - leadtime$$

Where filldate is the date to first fill the script as entered by the veterinarian. This could be the date the script created or a later date to account for sampling or other treatment factors involving delayed shipment such as to accommodate vacations of the customer, medication administered at the facility, and the like; fills is the original number of shipments ordered by the veterinarian; count is the current number of fills to be shipped; frequency is the interval between shipments in days; and leadtime is the time for shipping and handling in days or zero in the case of the first shipment to avoid a shipdate being a past date.

The foregoing formula is one example of how to calculate the shipdate, and it will be apparent to those of ordinary skill in the art that other formulas may be used to account for sampling of pills at the veterinarian's office or a more emergent need to start the animal on a treatment regimen requiring the client to visit a pharmacy in person. Further, it will be appreciated that there are a number of ways to calculate the appropriate shipdate for the autoship record generation process. Further, there are a number of potential factors that may be considered in determining what the proper shipdate will be, such as different carriers for shipment, different shipping distances, lead times for the carrier, packaging considerations, expiration dates of the products shipped and other metrics affecting or delaying shipment. Thus, the invention shall not be limited to the foregoing example, but shall include equivalent methods of determining the appropriate shipdate in accordance with the claims appended hereto.

Referring still to FIG. 6, at 1140, the current autoship record is complete, the order count is decremented and the new count is stored in the count field of the order in the orders database 1022. At 1150, count is determined, and if it is greater than zero, the steps 1120, 1130 and 1140 are repeated until the count has decremented to zero, a new autoship record being created for each iteration of the loop. If, upon determining the count, the count is zero, no further processing to create autoship records is required for this order.

At step 1160 the autoship generation process determines if there are more orders that require autoship processing. If not, all of the orders have been processed, and this aspect of the invention process terminates as shown at 1170. If there are still orders left, the autoship process retrieves the new order data for the new order found in the orders database, and the process repeats for the new order, and so forth until there are no more orders in the database to process.

Figure 7:
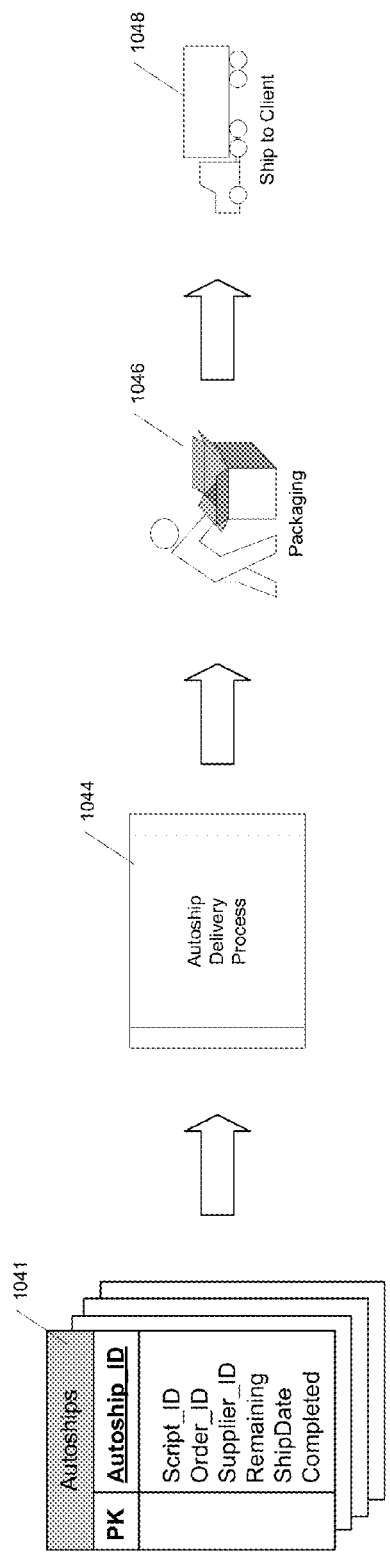
FIG. 7 is a schematic illustration of the process for completing delivery of orders in accordance with the autoship record generation aspect of the invention illustrated in FIGS. 5 and 6.
Figure 8:
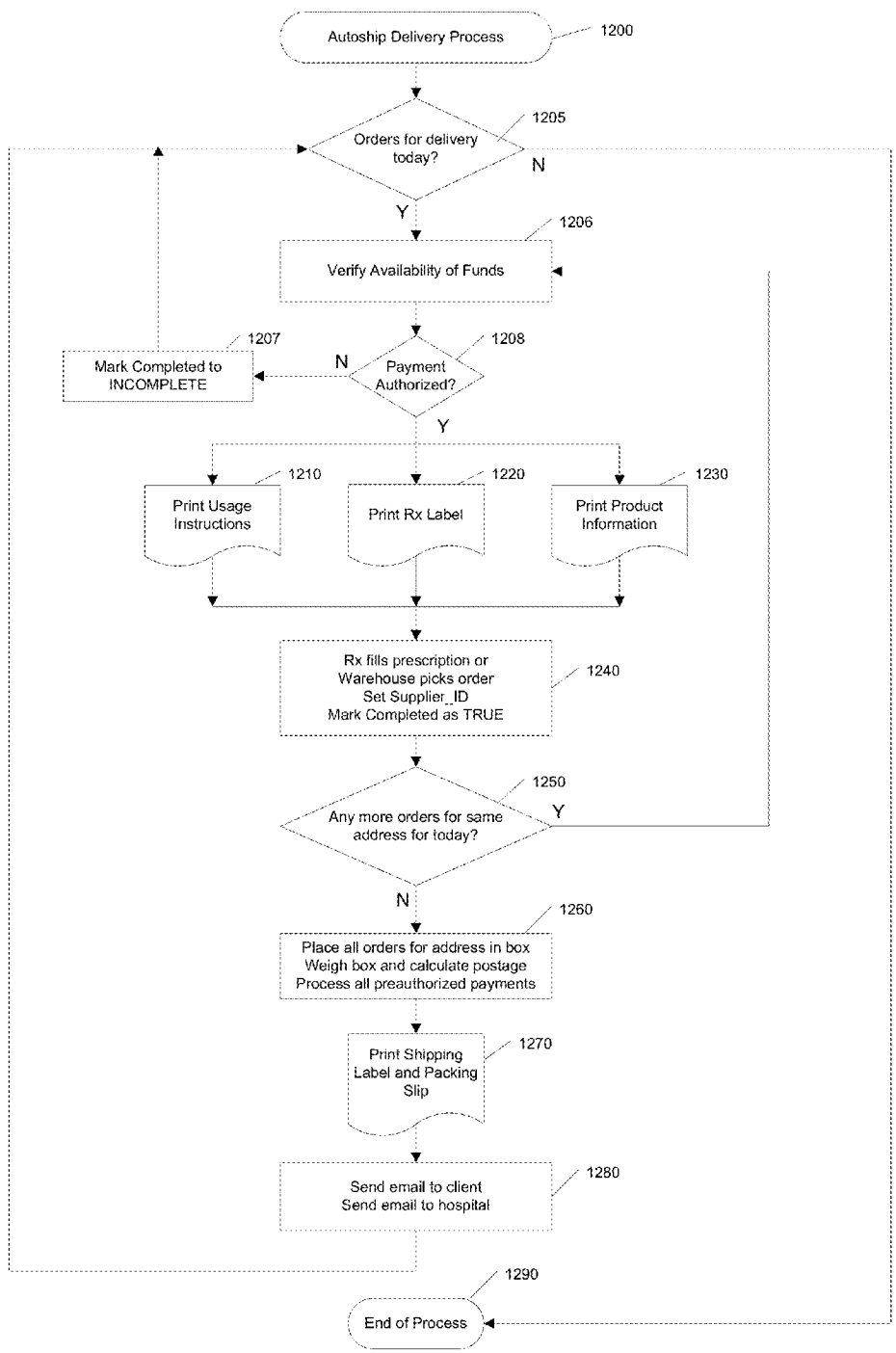
FIG. 8 shows a computer program flowchart of yet another aspect of the invention comprising the autoship delivery process of FIG. 7.

Referring to FIG. 7, a high level overview of the positioning of the autoship delivery process aspect of the invention, relative to the overall invention, is illustrated. Referring to FIG. 8, in the autoship delivery process aspect of the invention, autoship records that have matured, in that the shipdate of the autoship record has arrived, are selected for autoship delivery processing. In the autoship delivery process aspect of the invention, client funds are verified, usage instructions, Rx labels and product information are printed and prescriptions dispensed by a licensed pharmacist are packaged for shipping and shipped. If more than one product is to be shipped to a single client on the same day, multiple products may be packaged together for more economical shipping. It should be noted that, as with the autoship record generation process, the autoship delivery process is executed for all deliveries to be processed for all pets of all clients of all veterinarians from all of the hospitals registered in the system and who have products to be shipped as evidenced by matured autoship records in the database.

As shown in FIG. 8, the autoship delivery process begins as shown at 1200 at the beginning of a work day to allow shipment of products for all autoship records in the database for which the shipdate matches the current calendar date. At 1205, if there are no further orders for shipment on the current calendar date, there is no further autoship delivery process to execute and the program terminates as shown at 1290.

If there is an order to be delivered, billing information is used from client data that has been retrieved into computer readable medium to verify availability of funds for the client as shown at 1206 and 1208. If insufficient funds are available, the completed field of the autoship record is set to INCOMPLETE as shown at 1208 and 1207, the autoship record is returned to the autoship database, and the steps of the autoship delivery method are restarted at 1205 for a new record. If sufficient funds are verified at 1208, the autoship record is retrieved into computer readable medium as necessary to print usage instructions at 1210, to print an Rx label to be affixed to any medication container as indicated at 1220, and to print product information as shown at 1230 pertaining to the product from the product manufacturer. To perform the foregoing process, the system retrieves the order ID number to reference the script ID number, and its associated script record provides the hospital ID number, veterinarian ID number, client ID number and animal ID number. These ID numbers, in turn, are used to recall into computer readable medium the parts of the actual records associated with the various ID numbers which contain the details necessary for printing the usage instructions, the Rx labels and the shipping labels later on in the process. It will be appreciated that other information may be accessed, stored and printed at this point of the process as necessary or desirable.

Likewise, the system accesses the order ID number, which it references back to the product ID number, which is used in turn to retrieve at least part of the product record into computer readable medium including product information such as SKU number, supplier ID number, description, restrictions, controlled substance status and expiration information.

At 1240, documentation necessary is complete for the current autoship record, the remote pharmacy fills any prescription or the warehouse picks any other product, the supplier ID is set indicating the supplier used and the autoship completed field is marked as TRUE. At 1250, the autoship database is searched for any other autoship records for orders ready for shipping to the same address on the same day, thus enabling more economical processing of order shipping. If there are no more autoship records for orders to be shipped to that same address on that same day, then all products associated with the processed orders are packaged and weighed to calculate shipping charges as shown at 1260.

Thereafter, at 1270, a shipping label is printed from at least part of the data read into computer readable medium and affixed to the package for shipping, and as shown at 1280, an email notification is sent to the client, notifying them that the next supply of animal products has been shipped. Another email is sent to the hospital at this time, notifying staff that the medication has been shipped for delivery. The email notifications generated and sent in this step of the process serve to facilitate the client's compliance with the recommended treatment plan issued by the veterinarian.

Once the autoship delivery process is completed for all autoship records and orders associated with a particular address, the process loops back and is repeated for the next mature autoship record in the database.

Those of ordinary skill in the art will recognize that by using ID numbers in the autoship record, changes to relevant information about, for example, a client, such as his or her address change, will be reflected in the actual shipping delivery address since the shipment is created just in time based upon current information in the database. The address can be corrected at any location, such as at a client computer at a hospital, or even through an account access point at the customer's home online, to update the database to allow accurate shipping of the product at a time that is distant from the initial script (intervening changes between script generation and shipping).

It should also be apparent that having multiple autoship records allows more effective inventory control and projections of needed supplies as well as prediction of volumes of a particular product. While you could do this by looking at the database itself, performing this analysis at the autoship record level of the database is easier and more efficient because it involves simple ad hoc queries of that database to determine numbers of autoship records compared to needed numbers without requiring relational calculation requiring memory and system resources.

As shown at FIG. 3, one or more suppliers may be associated with any product, and the selection of a supplier may be facilitated with the use of metrics pulled from the system determined as described above, and this may be readily accomplished just in time at the time of dispensing and shipping of an order. Thus, if a particular supplier is desired because of external market factors, such as price or availability factors, that supplier may be selected to complete an order.

Further, at this point, the remote pharmacy may choose, for any of a number of reasons, to integrate a drop ship supplier, such as a supplier that ships product directly to a client at a request of the remote pharmacy, into the delivery process. For example, if the remote pharmacy does not have a particular medication in inventory, for the sake of the animal they may request a drop ship directly from the manufacturer directly to the client. Or, in another case, drop ship terms may involve a more favorable delivery process than keeping inventory of the product. In any case, whether to use a drop shipper, or not, would be at the discretion of the remote pharmacy.

While a preferred embodiment of the present invention has been shown and described, it will be apparent to those skilled in the art that many changes and modifications may be made without departing from the invention in its broader aspects. The appended claims are therefore intended to cover all such changes and modifications as fall within the true spirit and scope of the invention.

What is claimed is:

1. A computer-enabled method adapted for use in a computer system networked between an animal hospital and a remote central veterinary pharmacy for enabling veterinarians to generate veterinary medicine scripts and for generating corresponding orders for pre-scheduled automated processing, dispensing, fulfillment and delivery of veterinary medicine by the remote central veterinary pharmacy for delivery directly to the animal owner client in accordance with the script and orders, comprising the steps of:

registering the animal hospital with the remote central veterinary pharmacy;

retrieving and storing in a computer readable medium at least part of animal hospital data;

registering the veterinarian with the remote central veterinary pharmacy;

retrieving and storing in a computer readable medium at least part of veterinarian data;

retrieving and storing in a computer readable medium at least part of an animal owner client data profile;

retrieving, storing in a computer readable medium and displaying to a veterinarian at a networked client computer at the animal hospital at least part of an animal data profile;

enabling a licensed veterinarian at the networked client computer at the animal hospital in creating an electronic script comprising a reference to the animal hospital data retrieved, a reference to the veterinarian data retrieved, a reference to the client data retrieved, a reference to the animal data retrieved, veterinarian approval based on the veterinarian data retrieved, date of approval, and a complete status data field initially set to FALSE;

retrieving a list of available veterinary pharmaceutical products and displaying the list of available products to the veterinarian at the networked computer at the animal hospital;

enabling the veterinarian in selecting from the displayed list of veterinary pharmaceutical products a desired veterinary pharmaceutical product in accordance with animal data;

creating and storing to an orders database a plurality of electronic orders comprising a reference to the script, a reference to the selected pharmaceutical product and added pharmacy notes, usage instructions, initial fill date, quantity, fills, frequency and count data adapted for use in automatically generating a plurality of pre-scheduled autoship records; and approving the script as complete by setting a startdate data field to current date and the complete status data field to TRUE in the scripts database.

2. The computer-enabled method of claim 1, further comprising the following steps:

retrieving to computer readable medium an order from the orders database having a count greater than zero and that is associated with a script having a complete field set to TRUE;

creating and storing in a computer readable medium a unique autoship record having a unique autoship ID number;

retrieving at least a script ID number from the order and storing it into the autoship record;

retrieving at least an order ID number from the order record and storing it into the autoship record;

setting the supplier ID data field of the autoship record to zero;

setting the value in the remaining autoship record data field to count minus one;

calculating the ship date and storing the results in the shipdate field of the autoship record;

setting the completed data field of the autoship record to FALSE;

returning the autoship record to the autoship record database;

storing the value order count minus one in the count data field of the order record;

returning the updated order record to the orders database; and repeating the steps of the method until the count stored in the data field order count in the order record equals zero.

3. The computer-enabled method of claim 2, wherein the computer-calculated shipdate further comprises the following steps:

subtract the count from fills;
multiply the difference by the frequency;
subtract shipping lead time in days;
add the difference to the fill date; and
store the result as the shipdate for the current autoship record.

4. The computer-enabled method of claim 2, further comprising the steps of:

A. retrieving and storing in a computer readable medium an autoship record having a shipdate matching the current date and a completed field set to FALSE;

B. using billing information from the at least part of the data stored in the computer readable medium to verify availability of funds for client;
  (1) if insufficient funds are available, setting the completed field to INCOMPLETE and returning the autoship record to the autoship database;
  (2) if sufficient funds are available:
    (a) using the reference to the script to retrieve the reference to the animal hospital which is in turn used to retrieve and store in a computer readable medium at least part of the animal hospital data;
    (b) using the reference to the script to retrieve the reference to the veterinarian which is in turn used to retrieve and store in a computer readable medium at least part of the veterinarian data;
    (c) using the reference to the script to retrieve the reference to the client which is in turn used to retrieve and store in a computer readable medium at least part of the client data;
    (d) using the reference to the script to retrieve the reference to the animal which is in turn used to retrieve and store in a computer readable medium at least part of the animal data;
    (e) using the reference to the order to retrieve and store in a computer readable medium at least part of the order data;
    (f) using the reference to the order to retrieve the reference to the product which is in turn used to retrieve and store in a computer readable medium at least part of the product data;
    (g) printing usage instructions from at least part of the data stored in the computer readable medium;
    (h) printing an Rx label from at least part of the data stored in the computer readable medium;
    (i) printing product information from at least part of the data stored in the computer readable medium;
    (j) filling the prescription;
    (k) selecting a supplier from the suppliers database and setting the supplier ID in the autoship record;
    (l) setting the autoship record completed field to TRUE; and
    (m) returning the completed autoship record to the autoship database.

5. The computer-enabled method of claim 4, wherein the steps of the method are repeated for every autoship record in the database having associated matching client addresses and the shipdate matches the current date.

6. The computer-enabled method of claim 5, wherein each autoship record having an associated matching client address is placed in a single package, the package is weighed, postage is calculated, a shipping label is printed and a packing slip is printed.

7. The computer-enabled method of claim 4, further comprising the step of sending a notification email to at least one of the client and the hospital.

8. The computer-enabled method of claim 4, wherein the steps of the method are repeated for every autoship record in the database.

9. A computer-enabled method adapted for use in a computer system networked between a veterinarian and a remote central veterinary pharmacy for enabling veterinarians to generate veterinary medicine scripts and for generating corresponding orders for pre-scheduled automated processing, dispensing, fulfillment and delivery of veterinary medicine by the remote pharmacy for delivery directly to the animal owner client comprising the steps of:

registering the veterinarian with the remote central veterinary pharmacy;

retrieving and storing in a computer readable medium at least part of veterinarian data;

retrieving and storing in a computer readable medium at least part of an animal owner client data profile;

retrieving, storing in a computer readable medium and displaying to a veterinarian at a networked client computer at the animal hospital at least part of an animal data profile;

enabling a licensed veterinarian at the networked client computer at the animal hospital in creating an electronic script comprising a reference to the veterinarian data retrieved, a reference to the client data retrieved, a reference to the animal data retrieved, veterinarian approval based on the veterinarian data retrieved, date of approval, and a complete status data field initially set to FALSE;

retrieving a list of available veterinary pharmaceutical products and displaying the list of available products to the veterinarian at the networked computer at the animal hospital;

enabling the veterinarian in selecting from the displayed list of veterinary pharmaceutical products a desired veterinary pharmaceutical product in accordance with animal data;

creating and storing to an orders database a plurality of electronic orders comprising a reference to the script, a reference to the selected pharmaceutical product and added pharmacy notes, usage instructions, initial fill date, quantity, fills, frequency and count data adapted for use in automatically generating a plurality of pre-scheduled autoship records; and approving the script as complete by setting a startdate data field to current date and the complete status data field to TRUE in the scripts database.

10. The computer-enabled method of claim 9, further comprising the following steps:

retrieving to computer readable medium an order from the orders database having a count greater than zero and that is associated with a script having a complete field set to TRUE;

creating and storing in a computer readable medium a unique autoship record having a unique autoship ID number;

retrieving at least a script ID number from the order and storing it into the autoship record;

retrieving at least an order ID number from the order record and storing it into the autoship record;

setting the supplier ID data field of the autoship record to zero;

setting the value in the remaining autoship record data field to count minus one;

calculating the ship date and storing the results in the shipdate field of the autoship record;

setting the completed data field of the autoship record to FALSE;

returning the autoship record to the autoship record database;

storing the value order count minus one in the count data field of the order record;

returning the updated order record to the orders database; and repeating the steps of the method until the count stored in the data field order count in the order record equals zero.

11. The computer-enabled method of claim 10, further comprising the steps of:

retrieving and storing in a computer readable medium an autoship record having a shipdate matching the current date and a completed field set to FALSE;

using billing information from the at least part of the data stored in the computer readable medium to verify availability of funds for client;

if insufficient funds are available, setting the completed field to INCOMPLETE, returning the autoship record to the autoship database and restarting the steps of the method of claim 4;

if sufficient funds are available, using the reference to the script to retrieve the reference to the veterinarian which is in turn used to retrieve and store in a computer readable medium at least part of the veterinarian data;

using the reference to the script to retrieve the reference to the client which is in turn used to retrieve and store in a computer readable medium at least part of the client data;

using the reference to the script to retrieve the reference to the animal which is in turn used to retrieve and store in a computer readable medium at least part of the animal data;

using the reference to the order to retrieve and store in a computer readable medium at least part of the order data;

using the reference to the order to retrieve the reference to the product which is in turn used to retrieve and store in a computer readable medium at least part of the product data;

printing usage instructions from at least part of the data stored in the computer readable medium;

printing an Rx label from at least part of the data stored in the computer readable medium;

printing product information from at least part of the data stored in the computer readable medium;

filling the prescription;

selecting a supplier from the suppliers database and setting the supplier ID in the autoship record;

setting the autoship record completed field to TRUE; and returning the completed autoship record to the autoship database.

12. A computer-enabled method adapted for use in a computer system networked between an animal hospital and a remote central veterinary pharmacy for enabling veterinarians to generate veterinary medicine scripts and for generating corresponding orders for pre-scheduled automated processing, dispensing, fulfillment and delivery of veterinary medicine by the remote central veterinary pharmacy for delivery directly to the animal owner client in accordance with the script and orders, comprising the steps of:

registering the animal hospital with the remote central veterinary pharmacy;

retrieving and storing in a computer readable medium at least part of animal hospital data;

registering the veterinarian with the remote central veterinary pharmacy;

retrieving and storing in a computer readable medium at least part of veterinarian data;

retrieving and storing in a computer readable medium at least part of an animal owner client data profile;

retrieving, storing in a computer readable medium and displaying to a veterinarian at a networked client computer at the animal hospital at least part of an animal data profile;

enabling a licensed veterinarian at the networked client computer at the animal hospital in creating an electronic script comprising a reference to the animal hospital data retrieved, a reference to the veterinarian data retrieved, a reference to the client data retrieved, a reference to the animal data retrieved, veterinarian approval based on the veterinarian data retrieved, date of approval, and a complete status data field initially set to FALSE;

retrieving a list of available veterinary pharmaceutical products and displaying the list of available products to the veterinarian at the networked computer at the animal hospital;

enabling the veterinarian in selecting from the displayed list of veterinary pharmaceutical products a desired veterinary pharmaceutical product in accordance with animal data;

creating and storing to an orders database a plurality of electronic orders comprising a reference to the script, a reference to the selected pharmaceutical product and added pharmacy notes, usage instructions, initial fill date, quantity, fills, frequency and count data adapted for use in automatically generating a plurality of pre-scheduled autoship records;

approving the script as complete by setting a startdate data field to current date and the complete status data field to TRUE in the scripts database;

retrieving to computer readable medium an order from the orders database having a count greater than zero and that is associated with a script having a complete field set to TRUE;

creating and storing in a computer readable medium a unique autoship record having a unique autoship ID number;

retrieving at least a script ID number from the order and storing it into the autoship record;

retrieving at least an order ID number from the order record and storing it into the autoship record;

setting the supplier ID data field of the autoship record to zero;

setting the value in the remaining autoship record data field to count minus one;

calculating the ship date and storing the results in the shipdate field of the autoship record;

setting the completed data field of the autoship record to FALSE;

returning the autoship record to the autoship record database;

storing the value order count minus one in the count data field of the order record;

returning the updated order record to the orders database; and repeating the steps of the method until the count stored in the data field order count in the order record equals zero.

* * * * *